US006958211B2

(12) United States Patent
Vingerhoets et al.

(10) Patent No.: US 6,958,211 B2
(45) Date of Patent: Oct. 25, 2005

(54) METHODS OF ASSESSING HIV INTEGRASE INHIBITOR THERAPY

(75) Inventors: Johan Hendrika Jozef Vingerhoets, Wijnegem (BE); Lieve Emma Jan Michiels, Mol (BE); Inge Dierynck, Antwerp (BE)

(73) Assignee: Tibotech BVBA, Mechelen (BE)

( * ) Notice: Subject to any disclaimer, the term of this patent is extended or adjusted under 35 U.S.C. 154(b) by 88 days.

(21) Appl. No.: 10/215,158

(22) Filed: Aug. 8, 2002

(65) Prior Publication Data

US 2003/0124514 A1 Jul. 3, 2003

Related U.S. Application Data

(60) Provisional application No. 60/310,480, filed on Aug. 8, 2001.

(30) Foreign Application Priority Data

Aug. 8, 2001 (EP) .............................. 01203012

(51) Int. Cl.[7] ........................ C07H 21/02; C07H 21/04; C12Q 1/68; C12Q 1/70

(52) U.S. Cl. .............................. 435/5; 435/6; 435/7.1; 435/91.1; 435/91.2; 435/91.21; 435/91.3; 435/91.32; 435/91.33; 536/23.1; 536/24.3; 536/24.33

(58) Field of Search ...................... 435/5, 6, 7.1, 91.1, 435/91.2, 91.21, 91.3, 91.32, 91.33; 536/23.1, 24.3, 24.33

(56) References Cited

U.S. PATENT DOCUMENTS

| 5,202,259 A | 4/1993 | Goff et al. ............. 435/252.33 |
| 6,221,578 B1 | 4/2001 | de Bethune et al. |
| 6,562,575 B1 * | 5/2003 | Dahl .............................. 435/6 |
| 6,635,472 B1 * | 10/2003 | Lauermann ............... 435/320.1 |

FOREIGN PATENT DOCUMENTS

| WO | WO 94/16737 | 8/1994 |
| WO | WO 99/40227 | 8/1999 |
| WO | WO 99/67427 | 12/1999 |
| WO | WO 01/16860 A2 | 3/2001 |
| WO | WO 01/57245 A2 | 8/2001 |
| WO | WO 01/79540 A2 | 10/2001 |
| WO | WO 02/23186 A2 | 3/2002 |
| WO | WO 02/33402 A2 | 4/2002 |

OTHER PUBLICATIONS

Beorud, C. et al., "UMD (Universal Mutation Database): A generic Software to Build and Analyze Locus–Specific Databases", *Human Mutation*, Jan. 2000, 15(1), 86–94.
Boom, R. et al., "Rapid and Simple Method for Purification of Nucleic Acids", *Journal of Clinical Microbiology*, 1990, 28(3), 495–503.

De Leon, et al. "Clinical Feature . . . ", *Italian Journal of Gastroenterology and Hepatology*, Dec. 1999, 31(9), 850–860.
Harrigan, P.R.et al., "Baseline HIV Drug Resistance Profile Predicts Response to Ritonavir–Saquinavir Protease Inhibitor Therapy in a Community Settings", *AIDS*, 1999, 13, 1863–1871.
Hazuda, D.J. et al., "Inhibitors of Strand Transfer that Prevent Integration and Inhibit HIV–1 Replication in Cells", *Science*, 2000, 287, 645–650.
Hertogs, et al., "Comprehensive HIV Drug Resistance Monitoring Using Rapid, High–Throughput Phenotypic and Genotypic Assays with Correlative Data Analysis", *AIDS*, 1998, 12, Poster Abstracts OP3.4, ppS 11.
Hertogs, K. et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs" *Antimicrobial Agents and Chemotherapy*, 1998, 42(2), 269–276.
Jean pierre Cecile, et al., "Software and Database for the Analysis of Mutations in the Human WT1 Gene" *Nucleic Acids Research*, Jan. 1998, 26(1), 271–274.
Kellem, P. et al., "Recombinant Virus Assay: A Rapid, Pheotypic Assay for Assessment of Drug Susceptibility of Human Immunodeficiency virus Type 1 Isolates", *Antimicrobial Agents and Chemotherapy*, 1994, 38, 23–30.
Larder, B. et al., "A Complete Survey in Over 1,500 Clinical HIV–1 Isolates, of Phenotypic and Genotypic Protease Inhibitor Resistance Profiles (Including GAG Cleavage Site Sequences and Their Relation to Therapy History", *AIDS*, 1998, 12(4), S11.
Laurent–Puig Pierre, et al.,"APC Gene: Database of Germline and Somatic Mutations in Human Tumors and Cell Lines", *Nucleic Acids Research*, 1998, 26(1), 269–270.
Pauwels, R. et al., "Correlation Between Genotypic and Phenotypic Resistance Data in Avanti", *Abstracts of the Interscience Conference on Antimicrobial Agents and Chemotheraphy*, 1997, 37, 263–264.
Pauwels, R. et al., "Rapid and Automated Tetrazolium–Based Colorimetric Assay for the Detection of Anti–HIV Compounds" *Journal of Virological Methods*, 1988, 20, 309–321.
Petropoulos, C,J, et al., "Human Immunodeficiency Virus 1, Complete Genome" *Database Genbank NCBI*, 2000, Accession nr. NC_001802.

(Continued)

Primary Examiner—David Guzo
(74) Attorney, Agent, or Firm—Laura Donnelly

(57) ABSTRACT

Methods and products for the evaluation of HIV treatment are provided. The methods are based on evaluating molecular events at the HIV integrase resulting in altered therapeutic efficacy of tho investigated compounds. The methods rely on providing an integrase gene and evaluating either through integrase gene genotyping or phenotyping.

6 Claims, 1 Drawing Sheet

OTHER PUBLICATIONS

Figure 1:
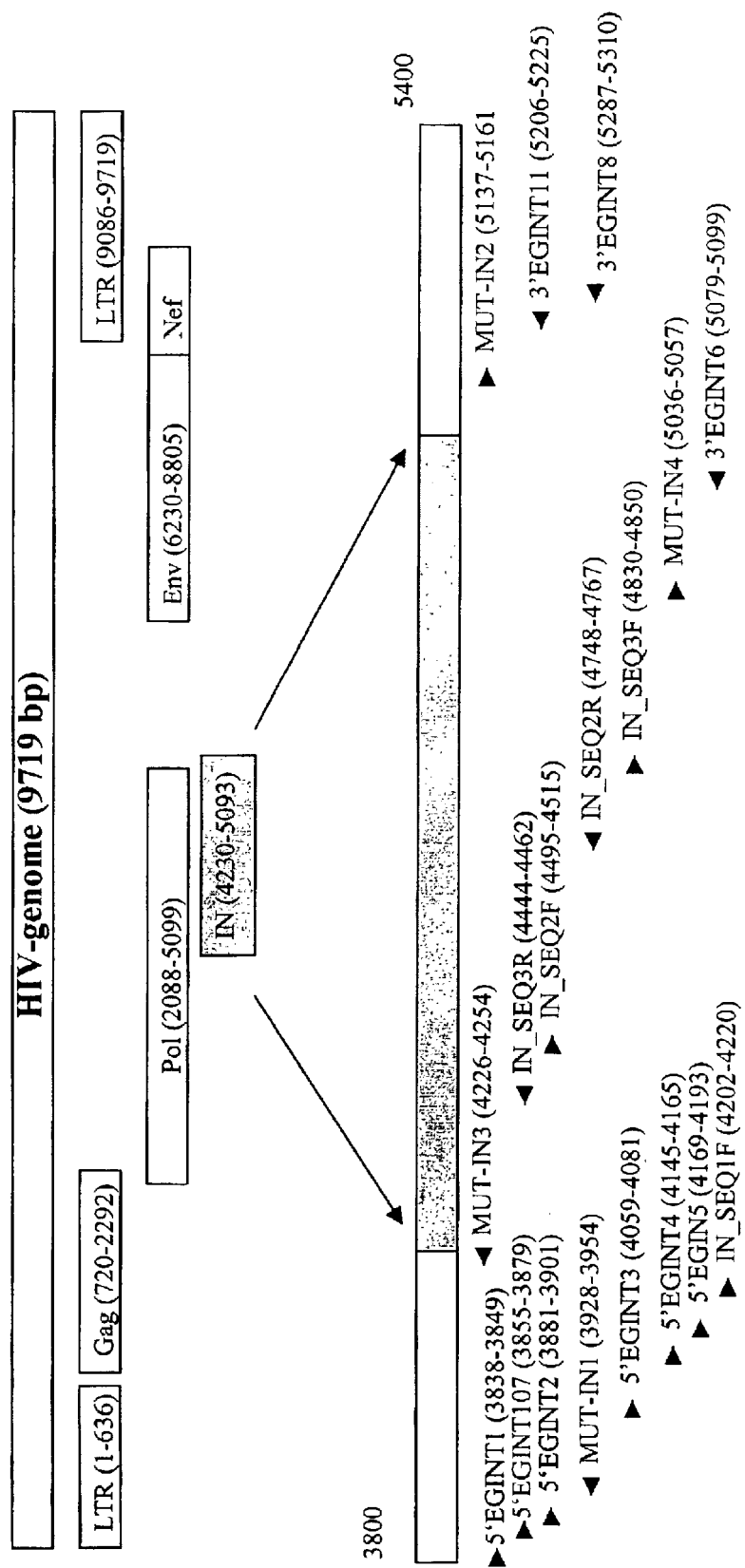

Vandamme, et al., "Managing Resistance to Anti–HIV Drugs–AN Important Consideration for Effective Disease Management", *Drugs*, 1999, 57(3), 337–361.

Water, H. et al., "Rapid, Phenotypic HIV–1 Drug Sensitivity Assay for Protease and Reverse Transcriptase Inhibitors", *Journal of Clinical Virolology*, 1999, 13, 71–80.

Wegner, S.A.et al.,"Prevalence of Genotypic and Phenotypic esistance to Anti–Retroviral Drugs in a Cohort of Therapy–Naïve HIV–1 Infected US Military Personnel", *AIDS*, 2000, 14, 1009–1015.

Woerner, A.M. et al., "Characterization of a DNA Binding Domain in the C–Terminus of HIV–1 Integrase by Deletion Mutagenesis", *Nucleic Acids Research*, 1993, 21(15), 3507–3511.

Ryan Reinke, et al., "Natural Selection Results in Conservation of HIV–1 Integrase Activity Despite Sequence Variability", AIDS 2001, vol. 15, No. 7, 2001, pp. 823–830.

Peter J. King, et al., "Resistance to the Anti–Human Immunodeficiency Virus Type 1 Compound L–Chicoric Acid Results from a Single Mutation at Amino Acid 140 of Integrase", Journal of Virology, vol. 72, No. 10, 1998, pp. 8420–8424.

NCBI Sequence Viewer Search of Nucleotide, Human Immunodeficiency virus 1, pp. 1–7, downloaded Nov. 19, 2002.

Martin S. Hirsch, et al., "Antiretroviral Drug Resistance Testing in Adult HIV–1 Infection", Consensus Statement, JAMA., vol. 283, No. 18, 2000, pp. 2417–2426.

A–M VanDamme, et al., "Laboratory Guidelines for the Practical Use of HIV Drug Resistance Tests in Patient Follow–Up", 2001, Antiviral Therapy, vol. 6, No. 21, pp. 21–39.

Lynn M. Skinner, et al., "Analysis of a Large Collection of Natural HIV–1 Integrase Sequences, Including Those From Long–Term Nonprogressors", Journal of Acquired Immune Deficiency Syndromes and Human Retrovirology, vol. 19, No. 2, 1998, pp 99–110.

* cited by examiner

METHODS OF ASSESSING HIV INTEGRASE INHIBITOR THERAPY

CROSS REFERENCE TO RELATED APPLICATIONS

This Application claims priority to U.S. Provisional Application Ser. No. 60/310,480, filed Aug. 8, 2001, and EP Application No. 01203012.8, filed Aug. 8, 2001, all of which are incorporated herein by reference in their entirety.

The present invention relates to methods and products for evaluating treatment of human immunodeficiency virus (HIV). In particular, molecular events at HIV integrase and their effect on therapeutic efficacy of drugs are determined. Suitably, the events are analysed by genotyping or phenotyping of HIV integrase. The methods and products described herein find use in multiple fields including diagnostics, drug screening, pharmacogenetics and drug development.

Several different treatment regimens have been developed to combat HIV infection. However, since the HIV virus is mutating quickly, because reverse transcriptase (RT) duplicating the genetic material has no proofreading capacity, it can counter the effects of drugs or drug combinations used against it. Current HIV chemotherapy involves inhibitors of the reverse transcriptase (RT) and protease enzymes. Despite the development of novel classes of inhibitors and complex drug regimens, drug resistance is increasing. Thus, new types of anti-HIV drugs are continually necessary. Development of compounds that inhibit other HIV gene products in vivo such as the envelope, tat, and integrase (IN) is a key area of investigation.

The integrase protein represents a target for HIV inhibitor research. HIV integrase is required for integration of the viral genome into the genome of the host cell, a step in the replicative cycle of the virus. It is a protein of about 32 KDa encoded by the pol gene, and is produced in vivo by protease cleavage of the gag-pol precursor protein during the production of viral particles. The integration process takes place following reverse transcription of the viral RNA. First, the viral integrase binds to the viral DNA and removes two nucleotides from the 3' end of the viral long-terminal repeat (LTR) sequences on each strand. This step is called 3' end processing and occurs in the cytoplasm within a nucleoprotein complex termed the pre-integration complex (PIC). Second, in a process called strand transfer, the two strands of the cellular DNA into which the viral DNA will be inserted, i.e. the target DNA, are cleaved in a staggered fashion. The 3' ends of the viral DNA are ligated to the 5' ends of the cleaved target DNA. Finally, remaining gaps are repaired, probably by host enzymes.

With the increasing number of available anti-HIV compounds, the number of potential treatment protocols for HIV infected patients will continue to increase. Many of the currently available compounds are administered as part of a combination therapy. The high complexity of treatment options coupled with the ability of the virus to develop resistance to HIV inhibitors requires the frequent assessment of treatment strategies. The ability to accurately monitor the replicative capacity of viruses in patients subjected to a drug regimen and to use that data to modify the doses or combinations of inhibitors allows physicians to effectively reduce the formation of drug resistant virus and provide an optimal, tailored treatment for each patient.

Sophisticated patient monitoring techniques have been developed for analysis of current therapies, e.g. such as Antivirogram®, (described in WO 97/27480 and U.S. Pat. No. 6,221,578 B1; incorporated herein by reference) and Phenosense™ (WO 97/27319). These cellular based assays determine the resistance of the patient borne virus towards a defined drug regimen by providing information about the susceptibility of the patient's virus strain to the treatment based on protease and reverse transcriptase inhibitors treatment. Other monitoring strategies include immunological means or sequencing techniques.

The Antivirogram® and Genseq™ assays determine the phenotype and genotype respectively of a patient's reverse transcriptase and protease genes. The relevant coding regions are obtained from patient samples, reverse transcribed and amplified by the polymerase chain reaction (PCR). Within lymphocyte cells the relevant coding regions are combined with viral deletion constructs to create chimeric viruses. The ability of these chimeric viruses to invade and kill cells in culture is assessed in the presence of HIV reverse transcriptase and protease inhibitors. A database combining phenotypic and genotypic information can be developed, as described in WO 00/73511 (incorporated herein by reference).

While phenotyping and genotyping assays such as Antivirogram® and Genseq™ have been developed for reverse transcriptase and protease genes, protocols for evaluation of drug resistance at the integrase gene have not been successfully developed.

DETAILED DESCRIPTION OF THE INVENTION

The instant invention provides techniques for evaluating human immunodeficiency (HIV) drug effectiveness. Assays for wild type or mutant HIV integrase are provided, using a set of primers designed for the amplification and analysis of HIV genetic material. The assessment of patient borne viral integrase leads to a better prediction of the drugs suitable for treatment of the strains present in the infected individual. The protocols and products may be used for diverse diagnostic, clinical, toxicological, research and forensic purposes including, drug discovery, designing patient therapy, drug efficacy testing and patient management. The assays described herein may be used in combination with other assays. The results may be implemented in computer models and databases. The products described herein may be incorporated into kits.

The instant invention relates to a method for determining the susceptibility of at least one HIV virus to at least one treatment, comprising: i) obtaining at least one sample of HIV RNA, wherein the sample comprises at least one IN gene or a portion thereof; ii) reverse-transcribing and amplifying the HIV RNA with primers specific for IN region of the HIV genome to obtain at least one DNA construct comprising the at least one IN gene or a portion thereof; iii) preparing at least one recombinant virus by homologous recombination or ligation between the amplified at least one DNA construct and a plasmid comprising the wild-type HIV sequence with a deletion in the IN region of the HIV genome, and iv) determining the phenotypic susceptibility of at least one HIV virus to at least one treatment by monitoring the at least one recombinant virus in the presence of the at least one treatment.

In particular, the present invention relates to a method for determining the susceptibility of at least one HIV virus to at least one drug, comprising: i) obtaining at least one sample comprising HIV RNA, wherein the sample comprises at least one IN gene or a portion thereof; ii) reverse transcribing and amplifying the HIV RNA with primers specific for IN region of the HIV genome to obtain at least one amplicon comprising the at least one IN gene or a portion thereof; iii) using nucleic acid amplification to generate a plasmid comprising the wild-type HIV sequence with a deletion in the IN region of the HIV genome; iv) preparing at least one recombinant virus by homologous recombination or ligation between the amplified at least one amplicon and a plasmid comprising the wild-type HIV sequence with a deletion in the IN region, and v) monitoring the at least one recombinant virus in the presence of the at least one treatment to determine the phenotypic susceptibility of at least one HIV virus to said at least one drug.

Reverse transcription and amplification may be performed with a single set of primers. Alternatively, more than one set of primers may be used in a hemi-nested approach to reverse transcribe and amplify the genetic material. Particularly, more than one set of primer is used in a nested approach. Following the generation of the recombinant construct, the chimeric virus may be grown and the viral titer determined (expressed as multiplicity of infection, MOI) before proceeding to the determination of the phenotypic susceptibility. The indicator gene, encoding a signal indicative of replication of the virus in the presence of a drug or indicative of the susceptibility of the virus in the presence of a drug may be present in the culturing cells such as MT-4 cells. In addition, said indicator gene may be incorporated in the chimeric construct introduced into the culturing cells or may be introduced separately. Suitable indicator genes encode fluorescent proteins, particularly green fluorescent protein or mutants thereof. In order to allow homologous recombination, genetic material may be introduced into the cells using a variety of techniques known in the art including, calcium phosphate precipitation, liposomes, viral infection, and electroporation. The monitoring may be performed in high throughput.

A human immunodeficiency virus (HIV), as used herein refers to any HIV including laboratory HIV strains, wild type HIV strains, mutant HIV strains and any biological sample comprising at least one HIV virus, such as, for example, an HIV clinical isolate. HIV strains compatible with the present invention are any such strains that are capable of infecting mammals, particularly humans. Examples are HIV-1 and HIV-2. For reduction to practice of the present invention, an HIV virus refers to any sample comprising at least one HIV virus. As for instance a patient may have HIV viruses in his body with different mutations in the integrase (IN) gene. It is to be understood that a sample may contain a variety of different HIV viruses containing different mutational profiles in the IN gene. A sample may be obtained for example from an individual, from cell cultures, or generated using recombinant technology, or cloning. HIV strains compatible with the present invention are any such strains that are capable of infecting mammals, particularly humans. Viral strains used for obtaining a plasmid are preferably HIV wild-type sequences, such as LAI or HXB2D. LAI, also known as IIIB, is a wild type HIV strain. One particular clone thereof, this means one sequence, is HXB2D. This sequence may be incorporated into a plasmid.

Instead of viral RNA, HIV DNA, e.g. proviral DNA, may be used for the methods described herein. In case RNA is used, reverse transcription into DNA by a suitable reverse transcriptase is needed. The protocols describing the analysis of RNA are also amenable for DNA analysis. However, if a protocol starts from DNA, the person skilled in the art will know that no reverse transcription is needed. The primers designed to amplify the RNA strand, also anneal to, and amplify DNA. Reverse transcription and amplification may be performed with a single set of primers. Suitably a hemi-nested and more suitably a nested approach may be used to reverse transcribe and amplify the genetic material.

Thus, the phenotyping method of the present invention may also comprise: i) obtaining at least one sample comprising HIV DNA, wherein the sample comprises at least one IN gene or a portion thereof; ii) amplifying the HIV DNA with primers specific for IN region of the HIV genome to obtain at least one amplicon comprising the at least one IN gene or a portion thereof; iii) generating a plasmid comprising the wild-type HIV sequence with a deletion in the IN region of the HIV genome characterized in that said deletion is generated using nucleic acid amplification; iv) preparing at least one recombinant virus by homologous recombination or ligation between the amplified at least one amplicon and a plasmid comprising the wild-type HIV sequence with a deletion in the IN region, and v) monitoring the at least one recombinant virus in the presence of the at least one drug to determine the phenotypic susceptibility of at least one HIV virus to at least one drug.

Nucleic acid may be amplified by techniques such as polymerase chain reaction (PCR), nucleic acid sequence based amplification (NASBA), self-sustained sequence replication (3SR), transcription based amplification (TAS), ligation chain reaction (LCR). Often PCR is used.

Any type of patient sample may be used to obtain the integrase gene, such as, for example, serum and tissue. Viral RNA may be isolated using known methods such as described in Boom, R. et al. (J. Clin. Microbiol. 28(3): 495–503 (1990)). Alternatively, a number of commercial methods such as the QIAAMP® viral RNA kit (Qiagen, Inc.) may be used to obtain viral RNA from bodily fluids such as plasma, serum, or cell-free fluids. DNA may be obtained by procedures known in the art (e.g. Maniatis, 1989) and commercial procedures (e.g. Qiagen).

The complete integrase (IN) or a portion of the IN gene may be used. The complete IN gene comprises 864 nucleotides (nt), coding for a 288 amino acid long integrase. A portion of the IN gene is defined as a fragment of IN gene recovered from patient borne virus, lab viruses including IIIB and NL4-3, or mutant viruses. This fragment does not encompass the complete 864 nt. Said fragment may be obtained directly from its source, including a patient sample, or may be obtained using molecular biology tools following the recovery of the complete IN sequence. Amplicon refers to the amplified, and where necessary, reverse transcribed integrase gene or portion thereof. It should be understood that this IN may be of diverse origin including plasmids and patient material. Suitably, the amplicon is obtained from patient material. For the purpose of the present invention the amplicon is sometimes referred to as "DNA construct". A viral sequence may contain one or multiple mutations versus the consensus reference sequence given by K03455. Said sequence, K03455, is present in Genbank and available through the internet. A single mutation or a combination of IN mutations may correlate to a change in drug efficacy. This correlation may be indicative of an altered i.e. decreased or increased susceptibility of the virus for a drug. Said mutations may also influence the viral fitness.

"Chimeric" means a construct comprising nucleic acid material from different origin such as for example a combination of wild type HIV with a laboratory HIV virus, a combination of wild type HIV sequence and patient derived HIV sequence.

A "drug" means any agent such as a chemotherapeutic, peptide, antibody, antisense, ribozyme and any combination thereof. Examples of drugs include protease inhibitors including ritonavir, amprenavir, nelfinavir; reverse transcriptase inhibitors such as nevirapine, delavirdine, AZT, zidovudine, didanosine; integrase inhibitors; agents interfering with envelope (such as for example T-20, T-1249). Treatment or treatment regimen refers to the therapeutic management of an individual by the administration of drugs. Different drug dosages, administration schemes, administration routes and combinations may be used to treat an individual.

An alteration in viral drug sensitivity is defined as a change in susceptibility of a viral strain to said drug. Susceptibilities are generally expressed as ratios of $EC_{50}$ or $EC_{90}$ values (the $EC_{50}$ or $EC_{90}$ value being the drug concentration at which 50% or 90% respectively of the viral population is inhibited from replicating) of a viral strain under investigation compared to the wild type strain. Hence, the susceptibility of a viral strain towards a certain drug can be expressed as a fold change in susceptibility, wherein the fold change is derived from the ratio of for instance the $EC_{50}$ values of a mutant viral strain compared to the wild type $EC_{50}$ values. In particular, the susceptibility of a viral strain or population may also be expressed as resistance of a viral strain, wherein the result is indicated as a fold increase in $EC_{50}$ as compared to wild type $EC_{50}$. The $IC_{50}$ is the drug concentration at which 50% of the enzyme activity is inhibited.

The susceptibility of at least one HIV virus to a drug may be tested by determining the cytopathogenicity of the recombinant virus to cells. In the context of this invention, the cytopathogenic effect means the viability of the cells in culture in the presence of chimeric viruses. The cells may be chosen from T cells, monocytes, macrophages, dendritic cells, Langerhans cells, hematopoetic stem cells or precursor cells, MT4 cells and PM-1 cells. Suitable host cells for homologous recombination of HIV sequences include MT4 and PM-1. MT4 is a $CD4^+$ T-cell line containing the CXCR4 co-receptor. The PM-1 cell line expresses both the CXCR4 and CCR5 co-receptors. All of the cells mentioned above are capable of producing new infectious virus particles upon recombination of the IN deletion vectors with IN sequences such as those derived from patient samples. Thus, they can also be used for testing the cytopathogenic effects of recombinant viruses. The cytopathogenicity may, for example, be monitored by the presence of any reporter molecule including reporter genes. A reporter gene is defined as a gene whose product has reporting capabilities. Suitable reporter molecules include tetrazolium salts, green fluorescent proteins, beta-galactosidase, chloramfenicol transferase, alkaline phophatase, and luciferase. Several methods of cytopathogenic testing including phenotypic testing are described in the literature comprising the recombinant virus assay (Kellam and Larder, Antimicrob. Agents Chemotherap. 1994, 38, 23–30, Hertogs et al. Antimicrob. Agents Chemotherap. 1998, 42, 269–276; Pauwels et al. J. Virol Methods 1988, 20, 309–321)

The susceptibility of at least one HIV virus to at least one drug may be determined by the replicative capacity of the recombinant virus in the presence of at least one drug, relative to the replicative capacity of an HIV virus with a wild-type IN gene sequence. Replicative capacity means the ability of the virus or chimeric construct to grow under culturing conditions. This is sometimes referred to as viral fitness. The culturing conditions may contain triggers that influence the growth of the virus, examples of which are drugs. The methods for determining the susceptibility may be useful for designing a treatment regimen for an HIV-infected patient. For example, a method may comprise determining the replicative capacity of a clinical isolate of a patient and using said replicative capacity to determine an appropriate drug regime for the patient. One approach is the Antivirogram® assay.

The IN phenotyping assays of the present invention can be performed at high throughput using, for example, a microtiter plate containing a variety of anti-HIV drugs. The present assays may be used to analyse the influence of changes at the HIV IN gene to any type of drug useful to treat HIV. Examples of anti-HIV drugs that can be tested in this assay include, nucleoside and non-nucleoside reverse transcriptase inhibitors, nucleotide reverse transcriptase inhibitors, protease inhibitors, membrane fusion inhibitors, and integrase inhibitors, but those of skill in the art will appreciate that other types of antiviral compounds may also be tested. The results may be is monitored by several approaches including but not limited to morphology screening, microscopy, and optical methods, such as, for example, absorbance and fluorescence. An $IC_{50}$ value for each drug may be obtained in these assays and used to determine viral replicative capacity in the presence of the drug. Apart from $IC_{50}$ also e.g. $IC_{90}$ or $EC_{50}$ (effective concentrations) can be used. The replicative capacity of the viruses may be compared to that of a wild-type HIV virus to determine a relative replicative capacity value. Data from phenotypic assays may further be used to predict the behaviour of a particular HIV isolate to a given drug based on its genotype.

The assays of the present invention may be used for therapeutic drug monitoring. Said approach includes a combination of susceptibility testing, determination of drug level and assessment of a threshold. Said threshold may be derived from population based pharmacokinetic modelling (WO 02/23186). The threshold is a drug concentration needed to obtain a beneficial therapeutic effect in vivo. The in vivo drug level may be determined using techniques such as high performance liquid chromatography, liquid chromatography, mass spectroscopy or combinations thereof. The susceptibility of the virus may be derived from phenotyping or interpretation of genotyping results i.e. virtual phenotyping (WO 01/79540).

The assays of the present invention may be useful to discriminate an effective drug from an ineffective drug by establishing cut-offs i.e. biological cut-offs (see e.g. WO 02/33402). A biological cut-off is drug specific. These cut-offs are determined following phenotyping a large population of individuals containing wild type viruses. The cut-off is derived from the distribution of the fold increase in resistance of the virus for a particular drug.

The instant invention also relates to a kit for phenotyping HIV integrase. Such kit, useful for determining the susceptibility of at least one HIV virus to at least one drug, may comprise: i) at least one of the primers selected from SEQ ID N°1–16, and ii) a plasmid as described in the present invention. For the purpose of performing the phenotyping assay, such kit may be further completed with at least one inhibitor. Optionally, a reference plasmid bearing a wild type HIV sequence may be added. Optionally, cells susceptible of HIV transfection may be added to the kit. In addition, at least one reagent for monitoring the indicator genes, or reporter molecules such as enzyme substrates, may be added.

The present invention also describes a method for determining the susceptibility of at least one HIV virus to at least one drug, comprising: i) obtaining at least one sample comprising HIV RNA, wherein the sample comprises at least one IN gene or a portion thereof; ii) reverse-transcribing and amplifying said HIV RNA with primers specific for the IN region of the HIV genome to obtain an amplicon comprising the IN gene or a portion thereof; iii) determining the nucleotide sequence of the amplicon or a portion thereof, and iv) comparing the nucleotide sequence of the amplicon to the sequence of known sequences to determine the susceptibility of at least one HIV virus to at least one drug. This assay protocol is commonly referred to as genotyping.

The genotype of the patient-derived IN coding region may be determined directly from the amplified DNA, i.e. the DNA construct, by performing DNA sequencing during the amplification step. Alternatively, the sequence may be obtained after sub-cloning into a suitable vector. A variety of commercial sequencing enzymes and equipment may be used in this process. The efficiency may be increased by determining the sequence of the IN coding region in several parallel reactions, each with a different set of primers. Such a process could be performed at high throughput on a multiple-well plate, for example. Commercially available detection and analysis systems may be used to determine and store the sequence information for later analysis. The nucleotide sequence may be obtained using several approaches including sequencing nucleic acids. This sequencing may be performed using techniques including gel based approaches, mass spectroscopy and hybridisation. However, as more resistance related mutations are identified, the sequence at particular nucleic acids, codons or short sequences may be obtained. If a particular resistance associated mutation is known, the nucleotide sequence may be determined using hybridisation assays (including Biochips, LipA-assay), mass spectroscopy, allele specific PCR, or using probes or primers discriminating between mutant and wild-type sequence. For these purposes the probes or primers may be suitably labelled for detection (e.g. Molecular beacons, TaqMan®, SunRise primers). Suitably, fluorescent or quenched fluorescent primers are used. The primer is present in a concentration ranging from 0.01 pmol to 100 pmol, suitably between 0.10 and 10 pmol. The cycling conditions include a denaturation step during 0.5 to 10 minutes, suitably, 1 to 5 minutes at a temperature ranging from 85 to 99° C. Interestingly, the temperature is between 90 and 98° C. Subsequently, the material is cycled during 14 to 45 cycles, suitably between 20 to 40 cycles, more suitably during 25 to 35 cycles. Nucleic acid is denatured at 90 to 98° C. during 5 seconds to 2 minutes. Suitably, denaturation periods range from 15 seconds to 1 minute. Annealing is performed at 40 to 60° C., specifically, between 45° C. and 57° C. The annealing period is 5 seconds to 1 minute, especially between 10 seconds and 35 seconds. Elongation is performed at 60° C. to 75° C. during 10 seconds to 10 minutes. Preferably, the elongation period is 15 seconds to 5 minutes. A selected set of sequencing primers includes SEQ ID 17–22. This particular selection has the advantage that it enables the sequencing of the complete HIV integrase gene. Consequently, using this set of primers all possible mutations that may occur in the HIV integrase gene may be resolved.

The patient IN genotype provides an additional means to determine drug susceptibility of a virus strain. Phenotyping is a lengthy process often requiring 2 or more weeks to accomplish. Therefore, systems have been developed which enable the prediction of the phenotype based on the genotypic results. The results of genotyping may be interpreted in conjunction with phenotyping and eventually be subjected to database interrogation. A suitable system is virtual phenotyping (WO 01/79540). In the virtual phenotyping process the complete IN genes may be used. Alternatively, portions of the genes may be used. Also combinations of mutations, preferentially mutations indicative of a change in drug susceptibility, may be used. A combination of mutations is sometimes referred to as a hot-spot (see e.g. WO 01/79540). Briefly, in the process of virtual phenotyping, the genotype of a patient derived IN sequence may be correlated to the phenotypic response of said patient derived IN sequence. If no phenotyping is performed, the sequence may be screened towards a collection of sequences present in a database. Identical sequences are retrieved and the database is further interrogated to identify if a corresponding phenotype is known for any of the retrieved sequences. In this latter case a virtual phenotype may be determined. A report may be prepared including the $EC_{50}$ of the viral strain for one or more therapies, the sequence of the strain under investigation, biological cut-offs.

The present invention also relates to a kit for genotyping HIV integrase. Such kit useful for determining the susceptibility of at least one HIV virus to at least one drug may comprise at least one primer selected from SEQ ID N° 1–12 and 17–22. Optionally, additional reagents for performing the nucleic amplification and subsequent sequence analysis may be added. Reagents for cycle sequencing may be included. The primers may be fluorescently labelled.

The instant invention provides a method of identifying a drug effective against HIV integrase comprising: i) obtaining at least one HIV integrase sequence, ii) determining the phenotypic response of the integrase towards said drug, iii) using said phenotypic response to determine the effectiveness of said drug. The phenotypic response is determined according to the methods of the instant invention.

The methods described in the instant invention may be used in a method of identifying a drug effective against HIV integrase comprising: i) obtaining at least one HIV integrase sequence, determining the sequence of said HIV integrase, ii) comparing said sequence with sequences present in a database of which the susceptibility has been determined of the HIV integrase, iii) using said sequence comparison to determine the effectiveness of said drug. The susceptibility and the sequence of the HIV integrase gene are determined according to the methods disclosed in the instant invention.

The genotyping and phenotyping methods as described herein can be used to create a genotypic and phenotypic database of IN sequences, comprising: i) obtaining samples comprising HIV RNA comprising the IN gene or a portion thereof; ii) reverse-transcribing and amplifying said HIV RNA with primers specific for the IN region of the HIV genome to obtain an amplicon comprising the IN gene or a portion thereof; iii) determining the nucleotide sequence of the amplicon or portions thereof; iv) generating a plasmid comprising the wild-type HIV sequence with a deletion in the IN region of the HIV genome characterized in that said deletion is generated using nucleic acid amplification; v) preparing recombinant virus by homologous recombination or ligation between the amplicon and a plasmid comprising the wild-type HIV sequence with a deletion in the IN region of the HIV genome, characterised in that said deletion is introduced using PCR; vi) determining the relative replicative capacity of the recombinant virus in the presence of anti-HIV drugs compared to an HIV virus with a wild-type IN gene sequence; vii) correlating the nucleotide sequence and relative replicative capacity in a data table.

According to the methods described herein a database may be constructed comprising genotypic and phenotypic data of the HIV integrase, wherein the database further provides a correlation between genotypes and between genotypes and phenotypes, wherein the correlation is indicative of efficacy of a given drug regimen. A database of IN sequences may be created and used as described in WO 01/79540. For example, such a database may be analysed in combination with pol and pro sequence information and the results used in the determination of appropriate treatment strategies. Said database containing a collection of genotypes, phenotypes and samples for which the combined genotype/phenotype are available may be used to determine the virtual phenotype (see supra). In addition, instead of interrogating the complete IN sequences, particular codons correlating to a change in drug susceptibility of the virus may be interrogated in such database.

A primer may be chosen from SEQ ID N° 1–23. A particular set of primers is SEQ ID 1–10, 13, 15, and 23. Primers specific for the IN region of the HIV genome such as the primers described herein and their homologs are claimed. The primer sequences listed herein may be labelled. Suitably, this label may be detected using fluorescence, luminescence or absorbance. The primer for creating a deletion construct may contain a portion that does not anneal to the HIV sequence. That portion may be used to introduce a unique restriction site. Interestingly, primers may be designed in which the unique restriction site is partially present in the HIV sequence. The primers are chosen from those listed herein or have at least 80% homology as determined by methods known by the person skilled in the art such BLAST or FASTA. Specifically, the homology is at least 90%, more specifically, at least 95%. In addition, primers located in a region of 50 nucleotides (nt) upstream or downstream from the sequences given herein constitute part of the invention. Especially, said region is 20 nucleotides up or downstream from the position in the HIV genome of the primer sequences given herein. Alternatively, primers comprising at least 8 consecutive bases present in either of the primers described here constitute one embodiment of the invention. Interestingly, the primers comprise at least 12 consecutive bases present in either of the primers described herein.

The present invention comprises the plasmids described in the experimental part and the use of the plasmids in the methods described herein. The HIV sequence incorporated in the plasmid may be based on the K03455 sequence. The complete HIV sequence may be incorporated or only part thereof. A suitable plasmid backbone may be selected from the group including pUC, pSV or pGEM.

A plasmid comprising a deleted integrase, wherein the deletion comprises at least 100 bp of the HIV integrase gene is provided herein. Suitably, more that 500 bp of the integrase gene are deleted, more suitably the complete IN gene is deleted. The deletion may also comprise parts of flanking genes, or eventually more than one gene, e.g. deletion of integrase and protease.

To prepare vectors containing recombinant IN coding sequences, the patient derived IN RNA can be reverse transcribed and amplified by the polymerase chain reaction (PCR), then inserted into a vector containing the wild type HIV genome sequence but lacking a complete IN coding region. Initially 36 different primer combinations were used to obtain amplified DNA sequences from 16 patient samples. The 5' to 3' sequences and the primers identified by SEQ ID's NO 1–10 of primers that can be successfully used to reverse transcribe and PCR amplify IN coding regions are listed below in Table 1.

A number of reverse transcription and PCR protocols known in the art may be used in the context of the present invention. A nested PCR approach to amplify the patient derived cDNA after reverse transcription may be used as described in Kellam, P. and Larder, B. A. , (Antimicrobial Agents and Chemotherapy 38: 23–30 (1994)), which is incorporated herein by reference. The nested approach of the instant invention utilizes two sets of primers, the outer primers are 5'EGINT1 (SEQ ID NO 1) and 3'EGINT 10 (SEQ ID NO 11), while the inner primers are 5'EGINT107 (SEQ ID NO 2) and 3'EGINT11 (SEQ ID NO 12). An additional inner 5' primer, 5'EGINT2 (SEQ ID NO 3), may also be used as a "rescue primer" to improve the yield of amplified DNA. Amplification using these primers yields a PCR product encompassing the complete IN coding sequence. Alternatively, 5'EGINT3 (SEQ ID NO 4) and 3'EGINT10 (SEQ ID NO 11) are used as outer PCR primers, while 5'EGINT4 (SEQ ID NO 5) or 5'EGINT5 (SEQ ID NO 6) and 3'EGINT6 (SEQ ID NO 7) are used as inner primers, yielding a PCR product encompassing a portion of the IN coding sequence.

TABLE 1

Primers for IN reverse transcription and PCR amplification.

| Primer Name | 5' to 3' sequence | SEQ ID NO |
|---|---|---|
| R-IN-vif and IN outer and inner primers | | |
| 5'EGINT1 | GGTACCAGTTAGAGAAAGAACCCA | SEQ ID NO:1 |
| 5'EGINT107 | GGAGCAGAAACCTTCTATGTAGATG | SEQ ID NO:2 |
| 5'EGINT2 | GGCAGCTAACAGGGAGACTAA | SEQ ID NO:3 |
| 5'EGINT3 | GGAATCATTCAAGCACAACCAGA | SEQ ID NO:4 |
| 5'EGINT4 | TCTGGCATGGGTACCAGCACA | SEQ ID NO:5 |
| 5'EGINT5 | AGGAATTGGAGGAAATGAACAAGTA | SEQ ID NO:6 |
| 3'EGINT6 | GTTCTAATCCTCATCCTGTCT | SEQ ID NO:7 |
| 3'EGINT7 | CCTCCATTCTATGGAGTGTCTATA | SEQ ID NO:8 |

TABLE 1-continued

Primers for IN reverse transcription and PCR amplification.

| Primer Name | 5' to 3' sequence | SEQ ID NO |
|---|---|---|
| 3'EGINT8 | GGGTCTACTTGTGTGCTATATCTC | SEQ ID NO:9 |
| 3'EGINT9 | CAGATGAATTAGTTGGTCTGCTA | SEQ ID NO:10 |
| 3'EGINT10 | CCT CCA TTC TAT GGA GAC TCC CTG | SEQ ID NO:11 |
| 3'EGINT11 | GCA TCC CCT AGT GGG ATG TG | SEQ ID NO:12 |
| R-IN-vif deletion-mutagenesis primers | | |
| MUT-IN1 | GGG TGA CAA CTT TTT GTC TTC CTC TAT | SEQ ID NO:13 |
| MUT-IN2 | <u>GGA TCC TGC AGC CCG</u> GGA AAG CTA GGG GAT GGT TTT ATA | SEQ ID NO:14 |
| IN deletion-mutagenesis primers: | | |
| MUT-IN3 | GGG CCT TAT CTA TTC CAT CTA AAA ATA GT | SEQ ID NO:15 |
| MUT-IN4 | <u>GGA TCC TGC AGC CCG</u> GGA TTA TGG AAA ACA GAT GGC A | SEQ ID NO:16 |
| Sequencing primers | | |
| IN_SEQ1F | AGT CAG TGC TGG AAT CAG G | SEQ ID NO:17 |
| IN_SEQ2F | TTC CAG CAG AAA CAG GGC AG | SEQ ID NO:18 |
| IN_SEQ3F | GTA GAC ATA ATA GCA ACA GAC | SEQ ID NO:19 |
| IN_SEQ1R | CCC TGA AAC ATA CAT ATG GTG | SEQ ID NO:20 |
| IN_SEQ2R | CTG CCA TTT GTA CTG CTG TC | SEQ ID NO:21 |
| IN_SEQ1R | TGA ACT GCT ACC AGG ATA AC | SEQ ID NO:22 |

The underlined portions do not anneal to the sequence to be amplified.

To prepare recombinant vectors comprising the amplified patient-derived IN sequences, these sequences can be inserted into vectors comprising the wild-type HIV sequence and a deletion of all or part of the IN coding region. The wild type HIV sequence can be obtained from a plasmid such as pSV40HXB2D that is capable of transfecting lymphocyte cells to produce viable virus particles. A deletion of the entire IN coding region on the pSV40HXB2D vector may effectively be created by PCR amplifying the plasmid using primers annealing to sequences at or near the ends of the IN coding region in the vector. The amplified product can be cleaved with a restriction enzyme introduced into the primers, then re-ligated to create a pSV40HXB2D-based IN deletion vector with a unique restriction site at the location of the deletion. The IN deletion vector can have a deletion of the complete IN coding sequence, optionally with part of the preceding RNase and/or subsequent Vif coding sequences also deleted. Alternatively, a partial deletion of the IN coding sequence is created. This restriction site is unique for the complete plasmid including the HIV gene. An example of such restriction site is the SmaI restriction site. Interestingly, the primers for creating a deletion construct are selected from SEQ ID N° 13–16.

Those of skill in the art will appreciate that several types of HIV vectors and cloning procedures known in the art may be used to create IN deletion plasmids for recombination or ligation with patient derived sequences and creation of infectious viruses. Generally, such vectors must be created to allow re-insertion of the deleted sequences without disrupting the reading frame of the gag-pol gene.

The amplified IN sequences may be inserted into the appropriate vector by homologous recombination between overlapping DNA segments in the vector and amplified sequence. Alternatively, the amplified IN sequence can be incorporated into the vector at a unique restriction site according to cloning procedures standard in the art. This latter is a direct cloning strategy.

EXPERIMENTAL PART

Example 1

Phenotyping HIV Integrase

1. PCR Amplification of Integrase Encoding Sequence

The integrase encoding sequence was amplified from either wildtype HIV-1 (IIIB) or NL4.3 virus, or HXB2D site-directed mutant viruses containing mutations in integrase (such as T66I, S153Y, M154I, or combinations thereof) (Hazuda et al., Science 2000, 287, 646–650), or patient samples. Starting from RNA, extracted from virus supernatant or plasma using the QIAamp® viral RNA extraction kit (Qiagen), cDNA was synthesized by reverse transcription (Expand™ reverse transcriptase, 30 min at 42°

C.) with the primer 3'EGINT10 (SEQ ID NO 11), followed by a nested PCR. The outer PCR was performed with the primers 5'EGINT1 (SEQ ID NO 1) and 3'EGINT10 (SEQ ID NO 11) (R-IN-vif construct) or 5'EGINT3 (SEQ ID NO 4) and 3'EGINT10 (SEQ ID NO 11) (IN construct) (Expand™ High Fidelity PCR system), and 5 μl of the outer product was used for an inner PCR with primers 5'EGINT2 (SEQ ID NO 3) and 3'EGINT11 (SEQ ID NO 12) (R-IN-vif construct) or 5'EGINT4 (SEQ ID NO 5) and 3'EGINT6 (SEQ ID NO 7) (IN construct). In a second protocol the outer primers were identical as described above, the inner primers are 5'EGINT5 (SEQ ID NO 6) and 3'EGINT6 (SEQ ID NO 7). The amplicons can be used for genotyping and phenotyping. Cycling conditions for both PCRs are denaturation for 3 min at 95° C., followed by 30 cycles of 1 min 90° C., 30 sec 55° C., and 2 min 72° C. A final extension was performed at 72° C. for 10 min. For recombination, PCR products are purified using the QiaQuick® 96 PCR BioRobot kit (Qiagen), according to the manufacturer's protocol. If the protocol starts from DNA containing the HIV material such as proviral DNA, the reverse transcriptase step is not needed. The nested approach is also not needed when starting from proviral DNA. The obtained amplicons were sequenced using the primers: In_seq1F (SEQ ID NO 17), In_seq2F (SEQ ID NO 18), In_seq3F (SEQ ID NO 19), IN_seq1R (SEQ ID NO 20), IN_seq2R (SEQ ID NO 21), and IN_seq3R (SEQ ID NO 22). The sequence of the IIIB and patient amplicon, and the NL4.3 amplicon were identical to the reference IIIB and NL4.3 sequences respectively (data not shown).

2. Preparation of a IN Deletion Construct

A R-IN-vif or IN deletion construct was generated by site-directed mutagenesis on the template pSV40HXB2D with the primers MUT-IN1 (SEQ ID NO 13) and MUT-IN2 (R-IN-vif construct) (SEQ ID NO 14) or MUT-IN3 (SEQ ID NO 15) and MUT-IN4 (SEQ ID NO 16) (IN construct) (protocol Site-directed mutagenesis kit, Stratagene). After DpnI digestion for removal of the methylated template DNA, the construct was digested with SmaI and ligated to circulize the plasmid. The plasmid was transformed into competent cells such as Top 10 cells, and colonies were screened for the presence of the deletion construct. The IN-deletion construct was checked by sequence analysis with primers 5'EGINT1 (SEQ ID NO 1) or 5'EGINT10 (SEQ ID NO 11) and 3'EGINT10 (SEQ ID NO 11) or 3'EGINT11 (SEQ ID NO 12). For use in recombination experiments, large-scale plasmid DNA preparations were linearized by SmaI digestion and recombined with PCR amplified integrase genes from wild type, mutant, or patient viruses. The plasmid containing the integrase deletion (IN) has been deposited pSV40HXB2D-IN. The sequence of said plasmid is 14377 nucleotides long. The R-IN-vif deletion construct is 13975 nucleotides long. The pSV40HXB2D-IN was deposited at the Belgian Coordinated Collections of Micro-Organisms located at the Universiteit Gent—Laboratorium voor Moleculaire Biologie on Aug. 5, 2002 and the accession number is LMBP 4574.

3. Recombination of Interase-amplified Sequences with the Corresponding Deletion Construct Recombinant virus was produced by co-transfection by electroporation of the SmaI-linearized IN-deletion construct and the integrase amplicon into MT4 cells or MT4 cells equipped with an LTR driven reporter gene construct. Production of recombinant virus was evaluated by scoring the cytopathogenic effect (CPE) that is induced by HIV-infection of MT4 cells or by the LTR-driven reporter signal induced by HIV infection in MT4 reporter cells. Green fluorescent protein was used as the reporter signal. Viruses are harvested and titrated at maximum CPE.

For recombination the deletion construct pSV40HXB2D-IN was used. Recombination experiments were performed with amplicon from wildtype HIV IIIB and NL4.3, and patient sample 146514 generated by both primer sets. For each recombination 2 μg amplicon was co-transfected with 10 μg SmaI-digested pSV40HXB2D- IN by electroportion into MT4-LTR-EGFP cells. Virus stocks were titrated and tested in an antiviral experiment on a reference panel including nucleoside reverse transcriptase inhibitors (NRTI), non-nucleoside reverse transcriptase inhibitors (NNRTI), protein inhibitor (PR), entry and integrase (IN) inhibitors (Table 2).

Recombination was checked by nucleic acid sequence analysis using protocols known to the person skilled in the art. Sequencing primers which can be used are In_seq1F (SEQ ID NO 17), In_seq2F (SEQ ID NO 18), In_seq3F (SEQ ID NO 19), IN_seq1R (SEQ ID NO 20), IN _seq2R (SEQ ID NO 21), and IN_seq3R (SEQ ID NO 22). The recombinant virus was evaluated in an anti-viral assay with a panel of reference compounds including nucleoside RT inhibitors (NRTI) Zidovudine (AZT) Lamivudine (3TC), Didanosine (DDI), non-nucleoside RT inhibitors (NNRTI) Nevirapine (NVP), 4-[[6-amino-5-bromo-2-[(4-cyanophenyl)amino]-4-pyrimidinyl]oxy]-3,5-dimethyl-benzonitrile also referred to as compound 1,4-[[6-amino-5-bromo-2-[(4-cyanophenyl)amino]-4-pyrimidinyl]oxy]-3,5-dimethyl-Benzonitrile, also referred to as compound 2 protease inhibitors (PR) Saquinavir (SQV), Amprenavir (APV), Indinavir (IDV), [(1S,2R)-3-[[(4-aminophenyl)sulfonyl](2-methylpropyl)amino]-2-hydroxy-1-(phenylmethyl) -propyl]-, (3R,3aS,6aR)-hexahydrofuro[2,3-b]furan-3yl ester carbamic acid also referred to as compound 3, entry-inhibitors (Entry)(AMD3100, DS5000, ATA), and integrase inhibitor (IN) 2-(1-methylethyloxy)- , -dioxo-5-(phenylmethyl)-benzenebutanoic acid also referred to as compound 4. The results are compiled in Table 2. AVE means antiviral experiment. Type means the type of inhibitor investigated. The fold change is the fold change in $EC_{50}$. WT III B means that a portion of the wild type IIIB strain has been amplified and used in the antiviral experiment, including transfection and generation of recombinant virus. NL 4-3 means the integrase gene of this laboratory strain has been amplified and subsequently used for the antiviral experiment. Patient 146514 means that the integrase gene of an HIV sample retrieved from said patient has been amplified and used in the antiviral experiment. pHXB2D has been used as a control. No recombination has been effected using this HIV clone. pHXB2D has been used directly for transfection and antiviral experiment. Primer set 3 consist of outer primers 5'EGINT3 (SEQ ID NO 4) and 3'EGINT10 (SEQ ID NO 11), and inner primers 5'EGINT4 (SEQ ID NO 5) and 3'EGINT6 (SEQ ID NO 7). Primer set 4 consist of outer primers 5'EGINT3 (SEQ ID NO 4) and 3'EGINT10 (SEQ ID NO 11), and inner primers 5'EGINT5 (SEQ ID NO 5) and 3'EGINT6 (SEQ ID NO 7). Other suitable integrase inhibitors include L-731,988, diketo-acids and S-1360.

The antiviral activity of these compounds against recombinant virus from wildtype HIV-1 IIIB or NL4.3 was identical to the activity against the HIV-1 IIIB and pHXB2D control strain, where no recombination has been performed. Recombinant virus generated from site-directed mutant virus gave a fold increase in $EC_{50}$ against compound 4 of respectively 2-fold (T66I mutation), 5-fold (S153Y), 3-fold (M154I mutation), 10-fold (T66I/ S153Y mutations or T66I/ M154I mutations). Recombinant virus generated from patient samples without mutations in the integrase coding sequence, displyed analogous results as the wildtype strains in the antiviral assay. The panel of protease and reverse transcriptase inhibitors were included in the list to prove that no background resistance, expressed as a fold increase in $EC_{50}$, was detected. The reverse transcriptase and protease genes present in the antiviral experiments were derived from wild type HIV sequence, which does not confer resistance to the drugs included. The instant results (Table 2) indicate that no change in susceptibility for any of these compounds is found.

TABLE 2

Antiviral experiment
Example 2 Genotyping of integrase
The methods and conditions used for sequence analysis of HIV integrase gene are outlined below. The sequencing primers (cfr. Table 1) cover the region of 864 nucleotides, from nucleotide 4230 until 5093 according to the sequence present in the HIV clone HXB2D. The sequencing primers were diluted until 1 pmol/µl and used in the mix and conditions as described below.

Reaction Mix

| Component | Reaction Mix |
| --- | --- |
| Big Dye Terminator Mix | 4 µl |
| 2.5 Dilution Buffer | 4 µl |
| Water | 4.8 µl |
| Primer (1 pmol/µl) | 3.2 µl |
| Sample (200–500 ng/µl) | 4 µl |
| TOTAL | 20 µl |

Thermal Cycle Conditions

| | | |
| --- | --- | --- |
| Initial Denaturation | 3' on 96° C. | |
| Denaturation | 30" on 96° C. | |
| Annealing | 15" on 50° C. | 30 cycles |
| Elongation | 4' on 60° C. | |
| | Hold on 4° C. | |

After cycle sequencing the reaction products were purified and run on the 3700 DNA analyzer.

Example 3

Construction of a Recombinant IN Vector
A) Construction of pSV40HXB2D R-IN-vif

The pSV40HXB2D R-IN-vif vector has a deletion of the complete IN coding sequence as well as part of the preceding RNase and subsequent Vif coding sequences. It was constructed by PCR amplification of pSV40HXB2D and religation of the amplified fragment. The primers used for amplification were MUT IN1 (5' GGG TGA CAA CTT TTT GTC TTC CTC TAT 3'; SEQ ID NO:13) and IN2 (5' GGA TCC TGC AGC CCG GGA AAG CTA GGG GAT GGT TTT ATA GA 3'; SEQ ID NO:23), which contain a SmaI site. Primer MUT IN1 (SEQ ID NO 13) anneals to nucleotides 3954 to 3928, and primer IN2 (SEQ ID NO 23) anneals to nucleotides 5137 to 5163. The first 14 nucleotides of IN2 (SEQ ID NO 23) comprise the Sma I tail, which does not anneal to the vector. The amplified product was cleaved with Sma I and re-ligated to create pSV40HXB2D R-IN-vif, with a Sma I recognition site at the location of the deletion.
B) Amplification of Patient Derived IN Sequences for Insertion into pSV40HXB2D R-IN-vif To amplify the complete IN coding region and the flanking segments of the RNase and Vif coding regions for insertion into the pSV40HXB2D R-IN-vif vector, a nested PCR method was used. The outer primers were 5'EGINT1 (SEQ ID NO 1) and 3'EGINT10 (SEQ ID NO 11), while the inner set was 5'EGINT107 (SEQ ID NO 2) and 3'EGINT11 (SEQ ID NO 12). An additional inner 5' primer, 5'EGINT2 (SEQ ID NO 3), was used to improve the yield of amplified DNA. (The sequences of these primers are given in Table 1, above.)
C) Construction of the pSV40HXB2D IN Vector To create pSV40HXB2D IN, the pSV40HXB2D vector was PCR amplified and re-ligated to effectively delete most of the IN coding region, leaving the nucleotides coding for the N-terminal 8 amino acids and the C-terminal 20 amino acids in place. The amplification was performed using the primers MUT IN3 (5' GGG CCT TAT CTA TTC CAT CTA AAA ATA GT 3'; SEQ ID NO:15) and MUT IN4 (5' GGA TCC TGC AGC CCG GGA TTA TGG AAA ACA GAT GGC A 3'; SEQ ID NO:16), containing a SmaI site. Primer MUT IN3 (SEQ ID NO 15) anneals to nucleotides 4254 to 4226, and primer MUT IN4 (SEQ ID NO 16) anneals to nucleotides 5 create 036 to 5057. The resulting amplified fragment can be cleaved with SmaI and re-ligated to pSV40HXB2D IN.
D) Amplification of Patient Derived IN Sequences for Insertion into pSV40HXB2D IN Patient derived IN sequences was prepared for insertion into the HIV deletion vector using a nested PCR approach as in part B above. 5'EGINT3 (SEQ ID NO 4) and 3'EGINT10 (SEQ ID NO 11) were used as outer PCR primers, while 5'EGINT4 (SEQ ID NO 5) or 5'3GINT5 (SEQ ID NO 6) and 3'EGINT6 (SEQ ID NO 7) were used as inner primers. The sequences and SEQ ID NO 4–8 of these primers are given in Table 1. The underlined portion of MUT IN4 (SEQ ID NO 16) represents the SmaI tail that does not anneal to the vector.
E) Homologous Recombination and Ligation to Insert the PCR Products into the Vectors The pSV40HXB2D IN or pSV40HXB2DAR-IN-vif vectors was linearized with SmaI. The vectors and the amplified IN DNA fragments were transfected by electroporation into MT4 cells, MT4 cells equipped with a LTR reporter gene construct (MT4-rep) or PM-1 cells. By homologous recombination between overlapping portions of the vector and IN amplicons, the HIV genome was reconstituted with a patient derived IN coding region. The recombinant vectors were capable of producing virus particles in infected cells. Virus production was evaluated by scoring the cytopathogenic effect (CPE) that was normally induced by HIV infection of MT4, MT4-rep, or PM-1 cells, or was evaluated by the induced LTR-driven reporter signal in MT4-rep or PM-1 cells. Homologous recombination with wild type IN sequences was used as a control.

The presence of recombinant IN DNA and RNA sequences in the transfected cells was monitored by reverse transcription and PCR analysis. The presence of PCR products corresponding to correctly inserted IN sequences showed that recombination successfully occurred and that viral RNA was produced in the cells.

Patient derived IN sequences and wild type controls were alternatively inserted into SmaI-linearized pSV40HXB2D N or pSV40HXB2D R-IN-vif vectors by a standard restriction digestion and ligation procedure. The IN amplicons were modified to create SmaI cleaved ends and were then inserted by ligation into the SmaI site on the vectors.

Example 4

Genotyping of Patient Derived IN Coding Sequences

A) Obtaining and Amplifying Patient Derived IN Sequences

RNA was isolated from 100 μl of plasma according to the method described by Boom et al. (1990), and reverse transcribed with the GENEAMP® reverse transcriptase kit (Perkin Elmer) as described by the manufacturer using an HIV-1 specific downstream primer. Two subsequent nested PCRs were set up using specific outer primers and inner primers, respectively. The outer primer reaction were performed as described in WO97/27480 and U.S. Pat. No. 6,221,578 (which are incorporated herein by reference). The inner amplification was performed in a 96 well plate as follows: 4 µl of the outer amplification product was diluted to a final volume of 50 µl using a 10× amplification mix consisting of 5 µl 10×PCR buffer containing 15 mM MgCl$_2$, 1 µl dNTP's (10 mM) 0.5 µl each primer (0.25 µg/ml), 0.4 µl EXPAND® High Fidelity polymerase (3.5 U/µl; Roche) and deionized water. Amplification was initiated after a short denaturation of the amplification product made using the outer primers (2 min at 94° C). Ten amplification cycles were run, each consisting of a 15 sec denaturation step at 94° C., a 30 sec annealing step at 60° C. and a 2 min polymerization step at 72° C. This amplification was immediately followed by 25 cycles consisting of a 15 sec denaturation step at 94° C., a 30 sec annealing step at 60° C. and a variable time polymerization step at 72° C. The polymerization step was initially run for 2 min and 5 sec, then was increased by 5 seconds in each cycle. Amplification was completed by an additional polymerization step of 7 min at 72° C. The reactions were held at 4° C. until further analysis or stored at −20° C. (for short periods) or −70° C. (for longer periods). The products can be analysed on DNA agarose gels and visualised by UV-detection. The products can be purified using the QIAQUICK® 96-well plate system as described by the manufacturer (Qiagen).

B. Sequencing of IN Coding Region

The IN coding region present on the amplified fragments were sequenced using techniques known in the art. The sequencing was started by first distributing 4 µl of the primer stocks (4.0 µM) over a 96 well plate where each stock was pipetted down the column. In a second step, master mixes were made consisting of 14 µl deionized water, 17.5 µl dilution buffer, 7 µl sample (PCR fragment) and 14 µl Big Dye™ Terminator Mix (Perkin Elmer). A fraction (7.5 µl) of each master mix, containing a specific PCR fragment, was transferred to a specific place into the 96 well plate so that each sample fraction was mixed with a different PCR primer set. Samples were pipetted across the rows. Samples were placed in a thermal cycler and sequencing cycles started. The sequencing reaction consisted of 25 repetitive cycles of 10 sec at 96° C., 5 sec at 50° C. and 4 min at 60° C., respectively. Finally, sequence reactions were be held at 4° C. or frozen until further analysis. The sequencing reactions were precipitated using a standard ethanol precipitation procedure, resuspended in 2 µl formamide and heated for 2 minutes at 92° C. in the thermal cycler. Samples were cooled on ice until ready to load. 1 µl of each reaction was loaded on a 4.25% vertical acrylamide gel in a 377 sequencer system and gel was run until separation of the fragments is complete.

C. Sequence Analysis of IN Coding Region

Sample sequences wer imported as a specific project into the sequence manager of Sequencher™ (Genecodes) and compared to the wild type reference sequence. Sequences were assembled automatically and set at 85% minimum match. Secondary peaks were searched and the minimum was set at 60%. Any sequence that extended beyond the 5' end or the 3' end of the reference were deleted. When a region of overlap between sequences from the same strand was reached, the poorest quality of sequence was deleted leaving an overlap of 5–10 bases. Ambiguous base calls were considered poor matches to exact base calls. The sequence assembly was saved within an editable contig.

Obtained sequences were edited to facilitate interpretation of the base calls. Ambiguous sequences were retrieved and checked for possible errors or points of heterogeneity. When the point of ambiguity appeared correct (both strands of sequence agreed but were different from the reference sequence) it was interpreted to be a variant. The reference sequence was used as an aid for building a contig and as a guide to overall size and for trimming. The reference sequence was not used for deciding base calls. A change was only made when both strands agreed. All gaps were deleted or filled, unless they occurred in contiguous groups of multiples of three (i.e., insertion or deletion of complete codons) based on data form both sequence strands. Once the editing was complete, the new contig sequence was saved as a consensus sequence and used for further analysis.

Detailed sequence editing was performed following certain rules: A) Applied Biosystems, Inc. primer blobs were trimmed at 5' ends where 1 consecutive base remained off the scale, the sequence was trimmed not more than 25% until the first 25 bases contained less than 1 ambiguity, at least the first 10 bases from the 5' end were removed, and B) 3' ends were trimmed starting 300 bases after the 5' trim, the first 25 bases containing more than 2 ambiguities were removed, the 3' end was trimmed until the last 25 bases contained less than 1 ambiguity. The maximum length of the obtained sequence fragment after trimming was 550 bases.

Sequences that failed to align were removed from the assembly and replaced by data retrieved from new sequence analyses. When further failures occur, PCR reactions were repeated. Chromatograms were visualised using an IBM software system.

Legends to the Figures

FIG. 1: Overview of the HIV genome indicating the primer positions

What is claimed is:

1. A method for determining the susceptibility of at least one HIV to at least one drug, comprising:
   i) obtaining at least one sample comprising HIV RNA from a patient, wherein the sample comprises at least one IN gene or a portion thereof;
   ii) reverse-transcribing and amplifying said HIV RNA with primers specific for the IN region of the HIV genome to obtain an amplicon comprising the IN gene or a portion thereof, wherein at least one primer is selected from SEQ ID NO: 1–12 and 17–22;
   iii) determining the nucleotide sequence of the amplicon or a portion thereof, and
   iv) comparing the nucleotide sequence of the amplicon to the sequence of known HIV sequences to estimate the susceptibility of at least one HIV to as least one drug.

2. A method for determining the susceptibility of at least one HIV to at least one drug, comprising:
   i) obtaining at least one sample comprising HIV DNA from a patient, wherein the sample comprise at least one IN gene or a portion thereof, wherein at least one primer is selected from SEQ ID NO: 1–12 and 17–22;

ii) amplifying said HIV DNA with primers specific for the IN region of the HIV genome to obtain an amplicon comprising the IN gene or a portion thereof;

iii) determining the nucleotide sequence of the amplicon or a portion thereof, and iv) comparing the nucleotide sequence of the amplicon to the sequence of know HIV sequences to estimate the susceptibility of at least one HIV to at least one drug.

3. A kit useful for determining the susceptibility of at least one HIV to at least one drug according to any claim 1 or 2, comprising at least one primer selected from SEQ ID NO: 1–12 and 17–22.

4. A primer as selected from SEQ ID NO 1–14.

5. A primer selected from SEQ ID NO 1–23.

6. A primer selected from SEQ ID NO 1–7 and SEQ ID NO 11–22.

* * * * *

UNITED STATES PATENT AND TRADEMARK OFFICE
CERTIFICATE OF CORRECTION

PATENT NO. : 6,958,211 B2 Page 1 of 1
APPLICATION NO. : 10/215158
DATED : October 25, 2005
INVENTOR(S) : Johan Hendrika Jozef Vingerhoets et al.

It is certified that error appears in the above-identified patent and that said Letters Patent is hereby corrected as shown below:

Column 24, Claim 2, Line 65, delete "comprise" and insert --comprises--.

Column 25, Claim 2, Line 8, delete "know" and insert --known--.

Signed and Sealed this

Twenty-sixth Day of December, 2006

JON W. DUDAS
*Director of the United States Patent and Trademark Office*

SEQUENCE LISTING

<160> NUMBER OF SEQ ID NOS: 23

<210> SEQ ID NO 1
<211> LENGTH: 24
<212> TYPE: DNA
<213> ORGANISM: Human immunodeficiency virus

<400> SEQUENCE: 1
ggtaccagtt agagaaagaa ccca                24

```
<210> SEQ ID NO 2
<211> LENGTH: 25
<212> TYPE: DNA
<213> ORGANISM: Human immunodeficiency virus

<400> SEQUENCE: 2
ggagcagaaa ccttctatgt agatg                                        25

<210> SEQ ID NO 3
<211> LENGTH: 21
<212> TYPE: DNA
<213> ORGANISM: Human immunodeficiency virus

<400> SEQUENCE: 3
ggcagctaac agggagacta a                                            21

<210> SEQ ID NO 4
<211> LENGTH: 23
<212> TYPE: DNA
<213> ORGANISM: Human immunodeficiency virus

<400> SEQUENCE: 4
ggaatcattc aagcacaacc aga                                          23

<210> SEQ ID NO 5
<211> LENGTH: 21
<212> TYPE: DNA
<213> ORGANISM: Human immunodeficiency virus

<400> SEQUENCE: 5
tctggcatgg gtaccagcac a                                            21

<210> SEQ ID NO 6
<211> LENGTH: 25
<212> TYPE: DNA
<213> ORGANISM: Human immunodeficiency virus

<400> SEQUENCE: 6
aggaattgga ggaaatgaac aagta                                        25

<210> SEQ ID NO 7
<211> LENGTH: 21
<212> TYPE: DNA
<213> ORGANISM: Human immunodeficiency virus

<400> SEQUENCE: 7
gttctaatcc tcatcctgtc t                                            21

<210> SEQ ID NO 8
<211> LENGTH: 24
<212> TYPE: DNA
<213> ORGANISM: Human immunodeficiency virus

<400> SEQUENCE: 8
cctccattct atggagtgtc tata                                         24

<210> SEQ ID NO 9
<211> LENGTH: 24
<212> TYPE: DNA
<213> ORGANISM: Human immunodeficiency virus

<400> SEQUENCE: 9
```

| | |
|---|---|
| gggtctactt gtgtgctata tctc | 24 |

<210> SEQ ID NO 10
<211> LENGTH: 23
<212> TYPE: DNA
<213> ORGANISM: Human immunodeficiency virus

<400> SEQUENCE: 10

| | |
|---|---|
| cagatgaatt agttggtctg cta | 23 |

<210> SEQ ID NO 11
<211> LENGTH: 24
<212> TYPE: DNA
<213> ORGANISM: Human immunodeficiency virus

<400> SEQUENCE: 11

| | |
|---|---|
| cctccattct atggagactc cctg | 24 |

<210> SEQ ID NO 12
<211> LENGTH: 20
<212> TYPE: DNA
<213> ORGANISM: Human immunodeficiency virus

<400> SEQUENCE: 12

| | |
|---|---|
| gcatcccta gtgggatgtg | 20 |

<210> SEQ ID NO 13
<211> LENGTH: 27
<212> TYPE: DNA
<213> ORGANISM: Human immunodeficiency virus

<400> SEQUENCE: 13

| | |
|---|---|
| gggtgacaac ttttttgtctt cctctat | 27 |

<210> SEQ ID NO 14
<211> LENGTH: 39
<212> TYPE: DNA
<213> ORGANISM: Human immunodeficiency virus

<400> SEQUENCE: 14

| | |
|---|---|
| ggatcctgca gcccgggaaa gctaggggat ggttttata | 39 |

<210> SEQ ID NO 15
<211> LENGTH: 29
<212> TYPE: DNA
<213> ORGANISM: Human immunodeficiency virus

<400> SEQUENCE: 15

| | |
|---|---|
| gggccttatc tattccatct aaaaatagt | 29 |

<210> SEQ ID NO 16
<211> LENGTH: 37
<212> TYPE: DNA
<213> ORGANISM: Human immunodeficiency virus

<400> SEQUENCE: 16

| | |
|---|---|
| ggatcctgca gcccgggatt atggaaaaca gatggca | 37 |

<210> SEQ ID NO 17
<211> LENGTH: 19
<212> TYPE: DNA
<213> ORGANISM: Human immunodeficiency virus

<400> SEQUENCE: 17

-continued

```
agtcagtgct ggaatcagg                                              19

<210> SEQ ID NO 18
<211> LENGTH: 20
<212> TYPE: DNA
<213> ORGANISM: Human immunodeficiency virus

<400> SEQUENCE: 18
ttccagcaga aacagggcag                                             20

<210> SEQ ID NO 19
<211> LENGTH: 21
<212> TYPE: DNA
<213> ORGANISM: Human immunodeficiency virus

<400> SEQUENCE: 19
gtagacataa tagcaacaga c                                           21

<210> SEQ ID NO 20
<211> LENGTH: 21
<212> TYPE: DNA
<213> ORGANISM: Human immunodeficiency virus

<400> SEQUENCE: 20
ccctgaaaca tacatatggt g                                           21

<210> SEQ ID NO 21
<211> LENGTH: 20
<212> TYPE: DNA
<213> ORGANISM: Human immunodeficiency virus

<400> SEQUENCE: 21
ctgccatttg tactgctgtc                                             20

<210> SEQ ID NO 22
<211> LENGTH: 20
<212> TYPE: DNA
<213> ORGANISM: Human immunodeficiency virus

<400> SEQUENCE: 22
tgaactgcta ccaggataac                                             20

<210> SEQ ID NO 23
<211> LENGTH: 41
<212> TYPE: DNA
<213> ORGANISM: Human immunodeficiency virus

<400> SEQUENCE: 23
ggatcctgca gcccgggaaa gctaggggat ggttttatag a                     41
```